United States Patent [19]
Helmlinger et al.

[11] 3,947,505
[45] Mar. 30, 1976

[54] 1-HALO-DODECA-TRI(TETRA)-ENE

[75] Inventors: Daniel Helmlinger, Dubendorf; Peter Naegeli, Wettingen, both of Switzerland

[73] Assignee: Givaudan Corporation, Clifton, N.J.

[22] Filed: Apr. 24, 1975

[21] Appl. No.: 571,186

Related U.S. Application Data

[62] Division of Ser. No. 337,341, March 2, 1973.

[52] U.S. Cl....... 260/654 R; 260/632 R; 260/593 R
[51] Int. Cl.².......................................... C07C 21/02
[58] Field of Search ................................ 260/654 R

[56] References Cited
FOREIGN PATENTS OR APPLICATIONS
233,538   5/1964   Austria............................ 260/654 R Primary Examiner—Delbert E. Gantz
Assistant Examiner—Joseph A. Boska
Attorney, Agent, or Firm—Thomas Cifelli, Jr.

[57] ABSTRACT

Flavorants and fragrance materials of the sinensal type, novel halides, alcohols, and ketones intermediates and process for making same.

3 Claims, No Drawings

1-HALO-DODECA-TRI(TETRA)-ENE

This is a division, of application Ser. No. 337,341 filed Mar. 2, 1973.

FIELD OF THE INVENTION

This invention relates to the fields of flavorants and fragrances.

SUMMARY OF THE INVENTION

This invention is concerned with a process for the manufacture of compounds of the sinensal type of the general formula $$\text{OHC}-\text{C}(\text{CH}_3)=\text{CH}-\text{CH}_2-\text{CH}_2-\text{C}(\text{CH}_3)=\lambda\text{CH}-\text{CH}_2-\text{A} \qquad (I)$$

wherein A represents a group of the formula $$-\text{CH}_2-\text{C}(=\text{CH}_2)-\text{CH}=\text{CH}_2 \quad \text{or}$$

$$-\text{CH}=\text{C}(\text{CH}_3)-\text{CH}=\text{CH}_2$$

An especially interesting compound of formula I manufactured in accordance with the present invention is trans-trans-2,6-dimethyl-10-methylene-dodeca-2,6,11-trienal ($\beta$-sinensal) which occurs in natural orange oil.

The process in accordance with the present invention for the manufacture of the compounds of formula I comprises oxidising a halide of the general formula $$\text{Hal}-\text{CH}_2-\text{C}(\text{CH}_3)=\text{CH}-\text{CH}_2-\text{CH}_2-\text{C}(\text{CH}_3)=\lambda\text{CH}-\text{CH}_2-\text{A} \qquad (II)$$

, wherein A has the significance given earlier and Hal stands for a chlorine or bromine atom.

The halide starting materials of formula II are novel and also form part of the present invention. They can be prepared, also in accordance with the present invention, by treating an alcohol of the general formula $$\text{H}_2\text{C}=\text{C}(\text{CH}_3)-\text{CHOH}-\text{CH}_2-\text{CH}_2-\text{C}(\text{CH}_3)=\lambda\text{CH}-\text{CH}_2-\text{A} \qquad (III)$$

, wherein A has the significance given earlier, with an appropriate halogenating agent.

The alcohols of formula III are also novel and form part of the present invention. They can be prepared, also in accordance with the present invention, by reducing a ketone of the general formula $$\text{H}_2\text{C}=\text{C}(\text{CH}_3)-\text{CO}-\text{CH}_2-\text{CH}_2-\text{C}(\text{CH}_3)=\lambda\text{CH}-\text{CH}_2-\text{A} \qquad (IV)$$

wherein A has the significance given earlier.

The ketones of formula IV are also novel and form part of the present invention. They can be prepared, also in accordance with the present invention, by the acidcatalysed reaction of a vinyl carbinol of the general formula $$\text{H}_2\text{C}=\text{C}(\text{CH}_3)-\text{CHOH}-\text{CH}_2-\text{A} \qquad (V)$$

, wherein A has the significance given earlier, with an enol ether of the general formula $$\text{H}_2\text{C}=\text{C}(\text{CH}_3)-\text{C}(\text{OR}^1)=\text{CH}_2 \qquad (VI)$$

, wherein $R^1$ represents a lower alkyl group, or a corresponding ketal of the general formula $$\text{H}_2\text{C}=\text{C}(\text{CH}_3)-\text{C}(\text{OR}^1)_2-\text{CH}_3 \qquad (VIII)$$

wherein $R^1$ has the significance given earlier.

DESCRIPTION OF THE PREFERRED EMBODIMENTS

The oxidation of a compound of formula II can be carried out according to methods known per se.

A preferred oxidation method comprises the treatment of a halide of formula Ii with an alkali salt of a primary or secondary nitroalkane; that is to say, of a compound which can form an aci-form. Examples of suitable nitroalkanes are nitromethane, nitroethane and 1- or 2-nitropropane, with 2-nitropropane being preferred and being used in the form of the sodium or potassium salt.

The oxidation can be carried out in the presence of anhydrous or aqueous organic solvents; for example, a unior polyvalent alcohol such as ethanol, isopropanol, tertbutanol or mono- or diethylene glycol, a water-soluble ether such as diethylene glycol ehtyl butyl ether, dioxan or tetrahydrofuran, a dialkyl amide such as dimethylformamide, an acetal such as methylal, a ketone such as acetone, acetonitrile etc. The oxidation components are preferably stirred in the solvent at a temperature between −10°C and 80°C. In a preferred embodiment of the process, a nitroalkane (e.g. 2-nitropropane) is dissolved in a mixture of an organic solvent (e.g. dimethylformamide, isopropanol or acetone) and aqueous sodium hydroxide or potassium hydroxide, a halide of formula II is added to the resulting solution of the sodium or potassium salt of the nitroalkane and the mixture is stirred with heating to about 50°–80°C. In another suitable embodiment of the process, a solution of an alkali alcoholate such as potassium tertbutylate in tertbutanol, can be added to a nitroalkane and the resulting solution or suspension of the alkali salt of the nitroalkane can be stirred with a halide of formula II at 0°–50°C. A nitroalkane can also be introduced into a suspension of finely divided anhydrous potassium hydroxide in an acetal such as methylal or an ether such as diethylene glycol ethyl butyl ether and the mixture obtained can be stirred with a halide of formula II at room temperature. Depending on the alkali salt and the solvent used, there is obtained a homogeneous solution or a mixture which separates into two layers. In the latter case, it is expedient to bring about an intimate mixture of the two phases by intensive stirring.

The halide starting materials of formula II are novel and also form part of the present invention. They can be prepared, also in accordance with the present invention, by treating an alcohol of the general formula $$\text{H}_2\text{C}=\text{C}(\text{CH}_3)-\text{CHOH}-\text{CH}_2-\text{CH}_2-\text{C}(\text{CH}_3)=\lambda\text{CH}-\text{CH}_2-\text{A} \qquad (III)$$

, wherein A has the significance given earlier, with an appropriate halogenating agent.

The treatment of an alcohol of formula III with an appropriate halogenating agent can be carried out in a manner known per se. Suitable halogenating agents include, for example, hydrogen halides (e.g. hydrogen bromide), phosphorus halides (e.g. phosphorus tribromide and phosphorus pentachloride) and thionyl chloride. Thionyl chloride is preferred.

The alcohols of formula III are also novel and form part of the present invention. They can be prepared, also in accordance with the present invention, by reducing a ketone of the general formula $$H_2C=C(CH_3)-CO-CH_2-CH_2-C(CH_3)=\atop CH-CH_2-A \quad (IV)$$

wherein A has the significance given earlier.

The reduction of the oxo group in a ketone of formula IV to a hydroxy group can be carried out in a manner known per se using a suitable reducing agent such as a complex alkali metal hydride (e.g. lithium aluminium hydride, sodium aluminium hydride or sodium borohydride), a complex trialkoxy-alkali metal hydride (e.g. trimethoxy lithium aluminium hydride or tritertbutoxy lithium aluminium hydride), a substituted aluminium hydride (e.g. diethyl aluminium hydride or diisobutyl aluminium hydride) or a trialkyl aluminium compound (e.g. triisopropyl aluminium). Complex alkali metal hydrides, especially lithium aluminium hydride, are preferred.

The reduction is expediently carried out in an organic solvent such as an ether (e.g. diethyl ether, dioxan or tetrahydrofuran).

It is advisable to carry out the reduction at a low temperature, that is to say at a temperature below room temperature (e.g. at 0°C).

The ketones of formula IV are also novel and form part of the present invention. They can be prepared, also in accordance with the present invention, by the acid-catalysed reaction of a vinyl carbinol of the general formula $$H_2C=C(CH_3)-CHOH-CH_2-A \quad (V)$$

, wherein A has the significance given earlier, with an enol ether of the general formula $$H_2C=C(CH_3)-C(OR^1)=CH_2 \quad (VI)$$

, wherein $R^1$ represents a lower alkyl group, or a corresponding ketal of the general formula $$H_2C=C(CH_3)-C(OR^1)_2-CH_3 \quad (VII)$$

wherein $R^1$ has the significance given earlier.

The lower alkyl groups denoted by $R^1$ in formulae VI and VII contain from 1 to 6 carbon atoms (e.g. the methyl, ethyl, isopropyl, tertbutyl and hexyl groups). The methyl group is the preferred lower alkyl group.

It is advantageous to use an excess of an enol ether of formula VI in the reaction, about 3 equivalents being sufficient from the practical point of view. If a corresponding ketal of formula VII is used instead of the enol ether, somewhat smaller yields of the desired ketone of formula IV are obtained.

The reaction is carried out in the presence of an acidic catalyst. As the acidic catalyst there is expediently used a strong mineral acid (e.g. sulphuric acid or phosphoric acid), an acidic salt (e.g. potassium bisulphate or pyridine hydrochloride), a strong organic acid (e.g. p-toluenesulphonic acid, oxalic acid and trichloroacetic acid) or a Lewis acid (e.g. zinc chloride or boron trifluoride etherate). The concentration of the acidic catalyst in the reaction mixture expediently amounts to about 0.01–1.0%, preferably about 0.1—0.3%.

The reaction can be carried out in the presence of or in the absence of a solvent. When a solvent is used, suitable solvents are, for example, hydrocarbons such as benzene, toluene, hexane, heptane, isooctane or petroleum ether. According to a particular embodiment, a portion of the solvent is distilled off during the reaction, the alcohol formed during the reaction distilling off therewith.

The reaction is preferably carried out at an elevated temperature; for example, at a temperature above 50°C and especially at the reflux temperature of the reaction mixture. The reaction can be carried out under normal pressure or under excess pressure. It is preferred to carry out the reaction under the atmosphere of an inert gas (e.g. nitrogen or argon).

The following Example illustrates the present invention:

Example a. A solution of 7 g of 2-methyl-6-methylene-octa-1,7-dien-3-ol and 14 g of 3,3-dimethoxy-2-methyl-1butene in 140 ml of toluene was heated in the presence of 140 mg of pyridine hydrochloride with stirring and under a nitrogen atmosphere for 45 minutes to 120°C, a mixture of methanol and toluene being slowly distilled off azeotropically. After cooling, the residue was washed with water, dried over anhydrous sodium sulphate and concentrated. The crude product (12.2g) was purified by chromatography on 250 g of silicagel. Using hexane/ether (95:5) there were eluted 4.9 g of pure trans-2,6-dimethyl-10-methylene-dodeca-1,6,11-trien-3-one; boiling point $_{0.01}$=55°–65°C; UV (ethanol): $\lambda_{max} = 220$ nm ($\epsilon = 23,000$).

This ketone can also be prepared as follows:

b. A solution of 10 g of 2-methyl-6-methylene-octa-1,7-dien-3-ol and 20 g of a mixture of 3,3-dimethoxy-2-methyl-1-butene and 2-methoxy-3-methyl-butadiene (1:1) in 100 ml of toluene was heated in the presence of 300 mg of potassium hydrogen sulphate with stirring and under an argon atmosphere for 30 minutes to 70°C and for 90 minutes to 100°–104°C, a mixture of methanol and toluene being slowly distilled off azeotropically After cooling, the mixture was filtered, the filtrate concentrated and the residue distilled under reduced pressure (0.01 mm Hg) at 55°–65°C in a bulb-tube. The product (8 g) was then purified by chromatography on 130 g of silicagel. By elution with hexane/ether (95:5) there were obtained 5.1 g of pure trans-2,6-dimethyl-10-methylene-dodeca-1,6,11-trien-3-one.

A solution of 9.8 g of trans-2,6-dimethyl-10methylene-dodeca-1,6,11-trien-3-one in 200 ml of ether was added dropwise to an ice-cooled solution of 3 g of lithium aluminium hydride in 200 ml of ether. The resulting mixture was heated for 3 hours to reflux and excess lithium aluminium hydride was decomposed by the addition of a saturated ammonium chloride solution. The mixture was then washed with water, dried and concentrated (yield 10.4 g). By chromatography on 200 g of silicagel there were obtained 5.8 g of pure trans-2,6-dimethyl-10-methylene-dodeca-1,6,11-trien-3-ol; boiling point $_{0.015} = 59°C$; UV (ethanol): $\lambda_{max} = 224$ nm ($\epsilon = 16,000$).

2.25 g of thionyl chloride were slowly added to a solution of 1.5 g of trans-2,6-dimethyl-10methylene-dodeca-1,6,11-trien-3-ol in 75 ml of dry ether. The mixture was left to stand overnight at room temperature, washed neutral with water, dried and concentrated. After column chromatography on 50 g of silicagel using hexane, there were obtained 1.2 g of pure trans-trans-1chloro-2,6-dimethyl-10-methylene-dodeca-2,6,11-triene; boiling point $_{0.025} =64°C$; UV (ethanol): $\lambda_{max} = 215$ nm ($\epsilon = 18,000$).

A solution of 1.7 g of potassium hydroxide in 2.7 ml of water was diluted with 17.5 ml of isopropanol and treated successively with 2.5 g of 2-nitropropane and 2 g of trans-trans-1-chloro-2,6-dimethyl-10-methylene-dodeca-2,6,11-triene. The mixture was heated for 30 minutes to 80°C, washed sucessively with 2-n sodium hydroxide, saturated sodium bicarbonate solution and saturated sodium chloride solution, dried over sodium sulphate and concentrated. The crude product (1.6g) was chromatographed on 90 g of silicagel. Using ether/hexane (5:95) there were eluted, in addition to 114 mg of an unidentified product, 600 mg of trans-trans-2,6-dimethyl-10-methylene-dodeca-2,6,11-trienal ($\beta$-sinensal); boiling point $_{0.02} = 43°C$; UV (ethanol): $\lambda_{max} = 225$ nm ($\epsilon = 28,400$).

What we claim is:

1. Halides of the general formula $$\text{Hal—CH}_2\text{—C(CH}_3\text{)=CH—CH}_2\text{—CH}_2\text{—C(CH}_3\text{)=} \\ \text{CH—CH}_2\text{—A} \quad\quad (II)$$

wherein A represents a group of the formula $$-\text{CH}_2-\text{C(=CH}_2)-\text{CH}=\text{CH}_2 \quad \text{or}$$

$$-\text{CH}=\text{C(CH}_3)-\text{CH}=\text{CH}_2 \quad \text{and}$$

Hal stands for a chlorine or bromine atom.

2. Compounds in accordance with claim 1, wherein Hal stands for a chlorine atom.

3. trans-trans-1-Chloro-2,6-dimethyl-10-methylene-dodeca-2,6,11-triene.

* * * * *

UNITED STATES PATENT OFFICE
CERTIFICATE OF CORRECTION

Patent No. 3,947,505      Dated March 30, 1975

Inventor(s) Daniel Helmlinger et al.      Page 1 of 3

It is certified that error appears in the above-identified patent and that said Letters Patent are hereby corrected as shown below:

Column 1, line 15,
"$OHC-C(CH_3)=CH-CH_2-CH_2-C(CH_3)=\lambda$
$CH-CH_2-A$"

should be -- $OHC-C(CH_3)=CH-CH_2CH_2-C(CH_3)=CH-CH_2-A$ --.

Column 1, line 32,
"$Hal-CH_2-C(CH_3)=CH-CH_2CH_2-C(CH_3)=\lambda$
$CH-CH_2-A$"

should be -- $Hal-CH_2-C(CH_3)=CH-CH_2-CH_2-C(CH_3)=CH-CH_2-A$ --.

Column 1, line 42,
"$H_2C=C(CH_3)-CHOH-CH_2-CH_2-C(CH_3)=\lambda$
$CH-CH_2-A$"

should be -- $H_2C=C(CH_3)-CHOH-CH_2-CH_2-C(CH_3)=CH-CH_2A$ --.

UNITED STATES PATENT OFFICE
CERTIFICATE OF CORRECTION

Patent No. 3,947,505  Dated March 30, 1975

Inventor(s) Daniel Helmlinger et al.

It is certified that error appears in the above-identified patent and that said Letters Patent are hereby corrected as shown below:

Column 2, line 56,
"$H_2C=C(CH_3)-CHOH-CH_2-CH_2-C(CH_3)=$ 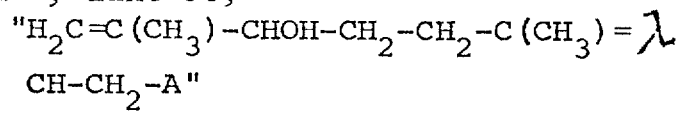
$CH-CH_2-A$"

should be - - $H_2C=C(CH_3)-CHOH-CH_2-CH_2-C(CH_3)=CH-CH_2-A$ - -.

Column 3, line 4,
"$H_2C=C(CH_3)-CO-CH_2CH_2-C(CH_3)=$ 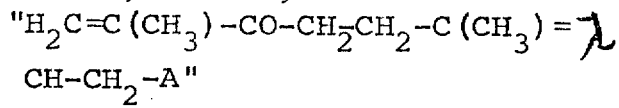
$CH-CH_2-A$"

should be - - $H_2C=C(CH_3)-CO-CH_2-CH_2-C(CH_3)=CH-CH_2A$ - -.

Column 6, line 4,
"$Hal-CH_2-C(CH_3)=CH-CH_2-CH_2-C(CH_3)=$ 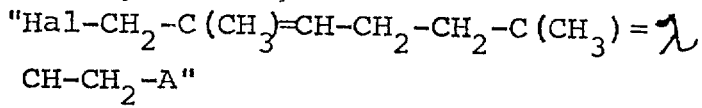
$CH-CH_2-A$"

should be - - $Hal-CH_2-C(CH_3)=CH-CH_2-CH_2-C(CH_3)=CH-CH_2-A$ - -.

Column 2, line 9,
"cut" should read - - out - -.

Column 2, line 11,
"Ii" should read - - II - -.

UNITED STATES PATENT OFFICE
CERTIFICATE OF CORRECTION

Patent No. 3,947,505   Dated   March 30, 1975

Inventor(s)   Daniel Helmlinger et al.   Page 3 of 3

It is certified that error appears in the above-identified patent and that said Letters Patent are hereby corrected as shown below:

Column 2, line 21,
"unior" should read - - uni-or - - .

Column 5, line 8,
"...2-n sodium . . ." should read - - ...2N sodium ... - - .

Signed and Sealed this

*twenty-ninth* Day of *June 1976*

[SEAL]

Attest:

RUTH C. MASON
*Attesting Officer*

C. MARSHALL DANN
*Commissioner of Patents and Trademarks*